US006575965B1

(12) United States Patent
Fitch et al.

(10) Patent No.: US 6,575,965 B1
(45) Date of Patent: Jun. 10, 2003

(54) MEDICAL DEVICES UTILIZING OPTICAL FIBERS FOR SIMULTANEOUS POWER, COMMUNICATIONS AND CONTROL

(75) Inventors: Joseph P. Fitch, Livermore, CA (US); Dennis L. Matthews, Moss Beach, CA (US); Karla G. Hagans, Livermore, CA (US); Abraham P. Lee, Arlington, VA (US); Peter Krulevitch, Pleasanton, CA (US); William J. Benett, Livermore, CA (US); Robert E. Clough, Danville, CA (US); Luiz B. DaSilva, Danville, CA (US); Peter M. Celliers, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 177 days.

(21) Appl. No.: 09/713,988

(22) Filed: Nov. 16, 2000

Related U.S. Application Data

(63) Continuation-in-part of application No. 09/373,511, filed on Aug. 12, 1999, now abandoned, which is a continuation of application No. PCT/US98/04020, filed on Mar. 2, 1998, which is a continuation of application No. 08/812,142, filed on Mar. 6, 1997, now Pat. No. 5,722,989.

(51) Int. Cl.⁷ ............................................. A61B 18/22
(52) U.S. Cl. ........................................ 606/15; 607/88
(58) Field of Search ...................... 606/15, 108; 607/88; 600/342

(56) References Cited

U.S. PATENT DOCUMENTS 5,370,649 A * 12/1994 Gardetto et al. ............... 606/17
5,498,260 A * 3/1996 Rink et al. ..................... 606/16
5,629,577 A    5/1997 Polla et al. .................... 310/328
5,700,260 A * 12/1997 Cho et al. ...................... 606/15
5,728,092 A * 3/1998 Doiron et al. .................. 606/15
5,730,700 A * 3/1998 Walther et al. ............... 600/104
5,769,791 A * 6/1998 Benaron et al. .............. 600/473
6,055,079 A    4/2000 Hagans et al. ............... 359/147
6,091,015 A * 7/2000 del Valle et al. ............. 136/243
6,095,974 A * 8/2000 Shemwell et al. ........... 600/310
6,102,917 A * 8/2000 Maitland et al. ............. 606/108

* cited by examiner

Primary Examiner—Kevin Shaver
Assistant Examiner—Michael B. Priddy
(74) Attorney, Agent, or Firm—L. E. Carnahan; Alan H. Thompson

(57) ABSTRACT

A medical device is constructed in the basic form of a catheter having a distal end for insertion into and manipulation within a body and a proximal end providing for a user to control the manipulation of the distal end within the body. A fiberoptic cable is disposed within the catheter and having a distal end proximate to the distal end of the catheter and a proximal end for external coupling of laser light energy. A laser-light-to-mechanical-power converter is connected to receive light from the distal end of the fiber optic cable and may include a photo-voltaic cell and an electromechanical motor or a heat-sensitive photo-thermal material. An electronic sensor is connected to receive electrical power from said distal end of the fiberoptic cable and is connected to provide signal information about a particular physical environment and communicated externally through the fiberoptic cable to the proximal end thereof. A mechanical sensor is attached to the distal end of the fiberoptic cable and connected to provide light signal information about a particular physical environment and communicated externally through the fiberoptic cable.

27 Claims, 12 Drawing Sheets

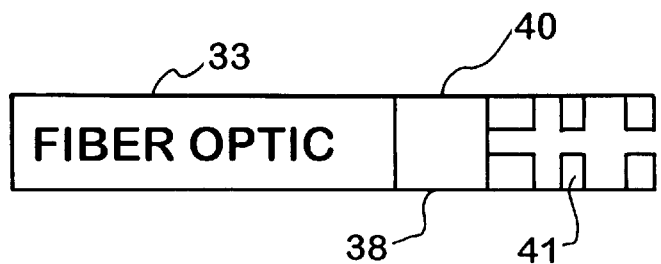
FIGURE 6
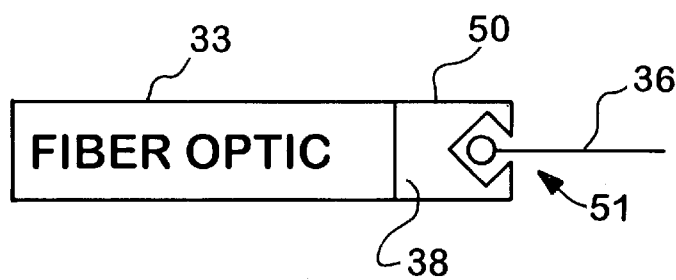
FIGURE 7
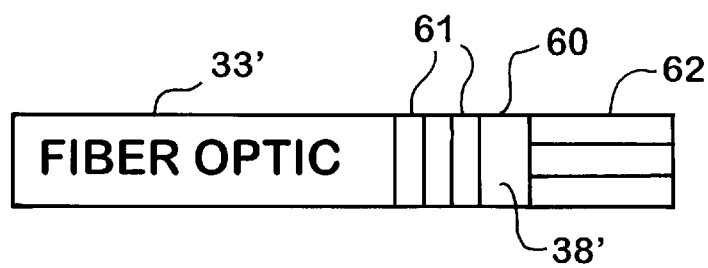
FIGURE 8
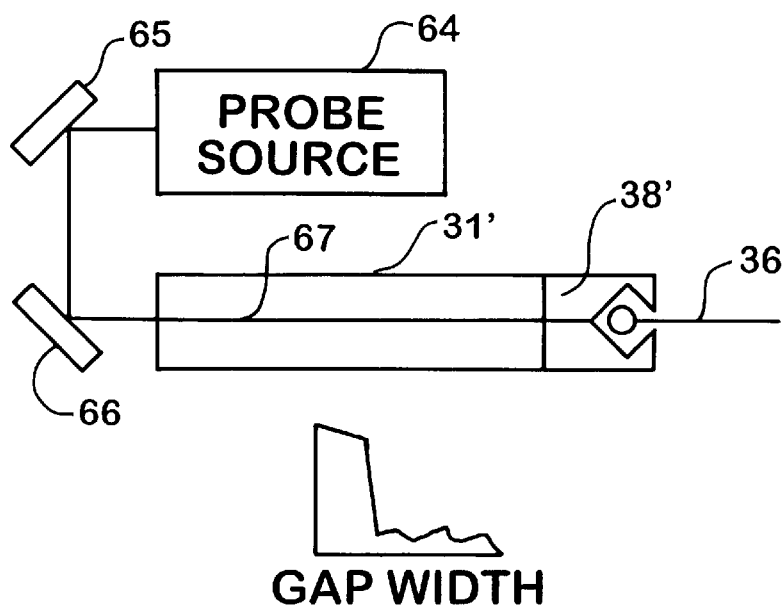
FIGURE 9A
FIGURE 9B

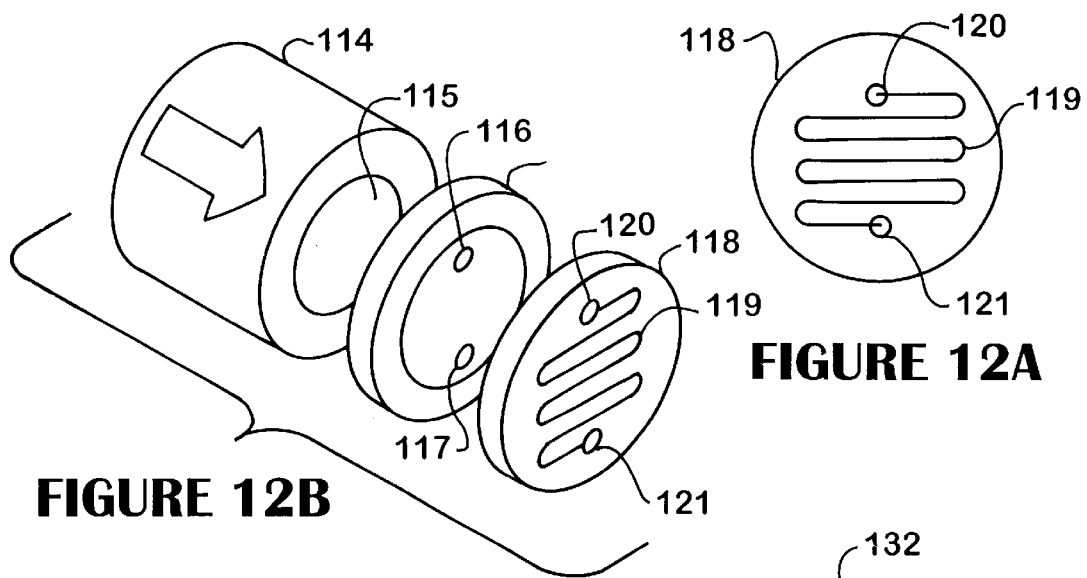
FIGURE 12B
FIGURE 12A
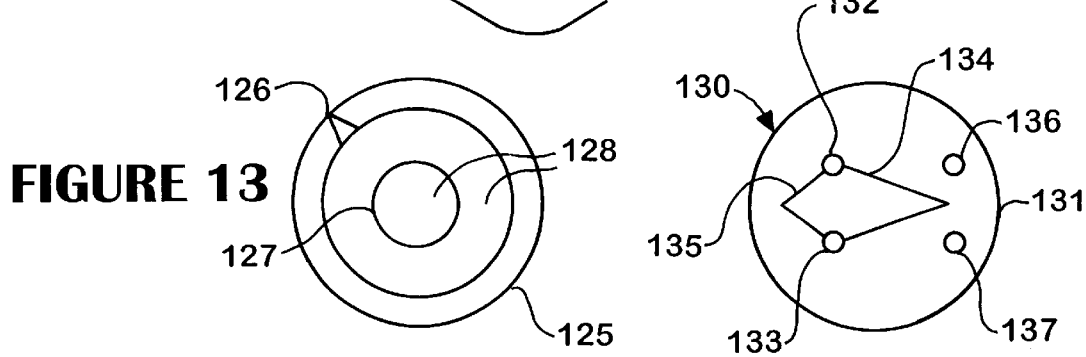
FIGURE 13
FIGURE 14A
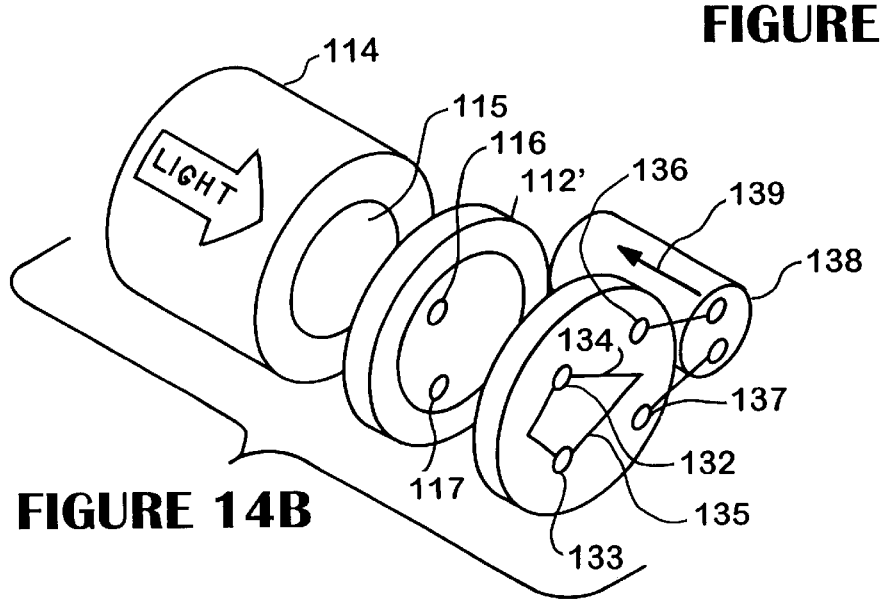
FIGURE 14B

MEDICAL DEVICES UTILIZING OPTICAL FIBERS FOR SIMULTANEOUS POWER, COMMUNICATIONS AND CONTROL

RELATED APPLICATIONS

This application is a continuation-in-part of U.S. application Ser. No. 09/373,511 filed Aug. 12, 1999, now abandoned, which is a continuation of International Applications No. PCT/US98/04020 filed Mar. 2, 1998, which is a continuation of U.S. application Ser. No. 08/812,142, filed Mar. 6, 1997, now U.S. Pat. No. 5,722,989 issued Mar. 3, 1998.

The United States Government has rights in this invention pursuant to Contract No. W-7405-ENG-48 between the United States Department of Energy and the University of California for the operation of Lawrence Livermore National Laboratory.

BACKGROUND OF THE INVENTION

The present invention relates to medical devices, particularly to medical devices with remote sensors and actuators, and more particularly to microminiaturized electromechanical devices for powering and controlling microgrippers mounted at a distal end of a catheter for medical application, or in a non-medical remote application, and which utilizes an optical fiber for simultaneously powering and controlling of the microgripper as well as communications relative to a physical environment of the microgripper.

In order to minimize patient discomfort and reduce healing time, the use of minimally invasive medical devices have increased rapidly. Reducing the size of these devices reduces the trauma even more.

Microactuators for remote and precise manipulation of small objects, such as coils to fill aneurysms in a blood vessel, have been under development for the past several years. These prior microgrippers and associated catheters, power sources etc, are exemplified by U.S. Pat. No. 5,609,608 issued Mar. 11, 1997; U.S. Pat. No. 5,645,564 issued Jul. 8, 1997; U.S. Pat. No. 5,771,902 issued Jun. 30, 1998; U.S. Pat. No. 5,911,737 issued Jun. 15, 1999; and U.S. Pat. No. 6,102,917 issued Aug. 15, 2000. There has been a need for a micromechanism which can position and release objects in small diameter, remote locations and which can communicate to a user, that the object has been positioned and released where intended.

The present invention satisfies the above mentioned need by providing a catheter-based micromniniaturized minimally invasive intravascular micromechanical system utilizing optical fibers for simultaneous power, communications and control. The system of the invention involves a catheter having a microgripper mounted at the distal end, a fiberoptic cable disposed within the catheter and having a distal end proximate to the distal end of the catheter and a proximal end coupled to laser light energy, a laser-light-to-mechanical and/or electrical-power converter connected to receive light from the distal end of the fiberoptic cable and connected to mechanically actuate the microgripper, and to power an electronic sensor to provide information about a particular physical environment in which the microgripper is located. Basically the present invention involves the use of optically driven mechanical and electronic based sensors and devices including acoustic mechanisms for converting optical energy to usable energy at the distal end or tip of the fiberoptic.

SUMMARY OF THE INVENTION

It is an object of the present invention to provide a medical device, which utilizes optical fibers for simultaneous power, communications, and control of the device.

A further object of the invention is to provide micromechanical systems for medical procedures.

A further object of the invention is to provide power (electrical, thermal, acoustic, optical, etc.) at the distal tip of a small catheter or device.

A further object of the invention is to eliminate MRI incompatible materials (magnetic materials) from a medical device.

A further object of the invention is the use of light to discern when an embolic material has been released from the delivery device (microgripper).

A further object of the invention is to reduce extraneous heating (at bends in wires, rotation induced effects, etc.) of the medical device.

A further object of the invention is to increase the communication bandwidth to the distal tip of a catheter or other device.

Another object of the invention a micro-mechanical system for medical procedures involving a catheter having a microgripper mounted to the distal end and having a fiberoptic cable disposed within the catheter with a distal end proximate to the distal end of the catheter, a laser-light-to-mechanical and/or electrical-power converter to actuate the microgripper, and an electronic, chemical and/or mechanical sensor to provide signal information about the physical environment of the microgripper.

Another object of the invention is to provide a micro-mechanical system for medical procedures, which involves the use of a photo-voltaic cell that generates electrical power and an electromechanical motor connected to actuate a microgripper mounted to a distal end of a catheter.

Another object of the invention is to provide a light-sensitive material or a heat-sensitive photo-thermal material mechanically connected to actuate a microgripper in response to light received via an optical fiber.

Another object of the invention is to provide an external "controller" that is necessary to operate and display/record information about the microgripper and sensors.

Other objects and advantages of the present invention will become apparent from the following description and accompanying drawings. The present invention involves the use of fiberoptics (5 to 400 micron diameter fibers) to replace wires and other electrical and mechanical devices currently used to power, communicate and/or control medical devices. Optical fibers have a variety of features (MRI compatible, small, flexible, easily manufactured, high bandwidth, variable bandwidths, etc.) that provide most of the existing features plus many new features for medical devices including optical power transmission, sensing, and communication. Some of the devices (motors) and sensors with electronic parts will have magnetic characteristics. Some capabilities are better suited for x-ray and other procedures. By providing modular energy conversion interfaces (photons to thermal chemical or electrical or mechanical or acoustic), at the distal tip of a fiber, medical, devices can be designed with greater utility and for less cost. One embodiment utilizes a photo-electric transducer whereby the electrical energy can be used to perform electronic, mechanical, drug delivery, and/or acoustic actions. Another embodiment involves the use of photo-thermal effects to directly control temperature-based shape memory devices for controlling a microgripper, for example. Also, various sensors can be utilized to provide information as to the environment in which a catheter mounted microgripper is located.

BRIEF DESCRIPTION OF THE DRAWINGS

The accompanying drawings, which are incorporated into and form a part of the disclosure, illustrate an embodiment of the invention and, together with the description, serve to explain the principles of the invention.

FIG. 6 schematically illustrates an electrically activated device, such as a shape memory alloy gripper, which incorporates a fiberoptic cable and a photo-electric transducer in accordance with the invention.

FIG. 7 schematically illustrates a mechanical device for retaining/releasing an embolic material form a microgripper, which incorporates a fiberoptic cable and a photo-thermal material.

FIG. 8 schematically illustrates a sensor array and a photo-electric transducer similar to FIG. 6.

FIGS. 9A and 9B schematically or graphically illustrate monitoring of reflected light from the apparatus of FIG. 7 showing the change in the gap between the fiberoptic and the embolic material, thereby assuring release of the material.

FIG. 12A is a view of a resistive heater embedded in a shape memory polymer.

FIG. 12B partially illustrates a fiber optic section similar to FIG. 11A with the resistive heater of FIG. 12A located adjacent the photo-voltaic section.

FIG. 13 illustrates an end view of a photo-voltaic section, similar to FIG. 11A but with concentric electrodes to reduce alignment complexity.

FIGS. 14A and 14B illustrates an optical fiber embodiment similar to FIG. 11A, but which incorporates a bridge electrical element (FIG. 14A) to measure electrical impedance of the exposed distal tip to provide communication from the distal tip to the user.

DETAILED DESCRIPTION OF THE INVENTION

Figure 1A:
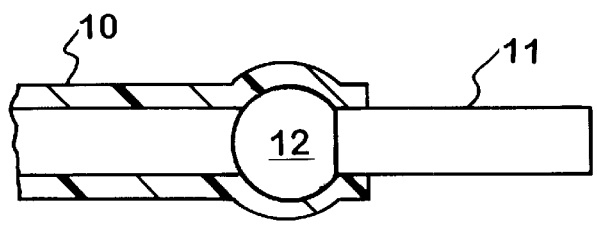
FIGS. 1A and 1B illustrate a prior art microgripper that utilizes a shape memory polymer tube to retain and release an object.

The present invention is directed to the use of optical fibers for simultaneous power, communication and control in medical devices. The invention involves remote sensors and actuators particularly for microminiaturized electromechanical microgrippers for use in catheter-based interventional therapies or in non-medical remote micro-assembly applications, having very small access ports and very small operational diameter areas that are buried deep within a body or assembly.

The invention can be summarized as providing energy conversion interfaces. Since so many miniaturized systems currently take electricity as the energy input, this appears to be the most valuable interface. A photo-voltaic, for example, is used to convert optical energy to electrical energy. The medical benefits include those listed above as well as isolating the device from "wall plug" electrical direct energy sources. In fact, if a battery is used to power the device, the regulatory requirements are significantly reduced.

The invention also involves an external "controller" that is necessary to operate and display/record information about the microgripper and sensors. The "controller" can be utilized in a number of ways, and can include: 1) battery or AC powered, 2) integral display screens or connected to a PC with monitor, and 3) contains driving and controlling lasers.

In the hereinafter-illustrated embodiments, single optical fibers are illustrated for simplicity, but a number of optical fibers may be utilized. In view of the small diameters of optical fibers, size and flexibility do not seem to be issues in such devices.

One embodiment of the present invention is a micromechanical system for medical procedures. The system is constructed in the basic form of a catheter having a distal (tip) end for insertion into and manipulation within a body and a proximal (near) end providing for a user to control the manipulation of the distal end within the body. A fiberoptic cable is disposed within the catheter and has a distal end proximate to the distal end of the catheter and a proximal end for external coupling of laser light energy. A microgripper is attached to the distal end of the catheter and provides for the gripping or releasing of an object, such as a deposit material (embolic coil), within the body. A laser-light-to mechanical-power converter is connected to receive light from the distal end of the fiberoptic cable and is connected to actuate the microgripper. The system of the invention includes sensors (electrical, thermal, mechanical) connected to the distal end of the fiberoptic cable to provide signal information about the release of an object or the desired physical environments in which the microgripper is located and internally communicated through the fiberoptic cable to a user. These physical environments include at least one of gap distance from microgripper to object, pH, chemistry, position, wall elasticity, acceleration, pressure, temperature, local flow rate, ambient light, ambient sound, and video image. The laser-light-to mechanical-power converter may include: 1) a photo-voltaic cell that generates electrical power in response to laser light received by the fiberoptic cable, and an electromechanical motor or transducer connected to actuate the microgripper; 2) a heat-sensitive material, such as photo-thermal material, is connected to actuate the microgripper in response to laser light received by the fiberoptic cable at its proximal end which is conducted to its distal end; and 3) a capacitor electrically connected to discharge in to an electromechanic motor connected to the microgripper in response to laser light received by the fiberoptic cable at its proximal end and conducted to its distal end, such that the electromagnetic motor actuates the microgripper.

The invention uses fiber optics (5 to 400 micron diameter fibers) to replace wires and other electrical and mechanical devices that are currently used to power, communicate and/or control medical devices. Optical fibers have a variety of features (MRI compatible, small, flexible, easily manufactures, high bandwidth, variable wavelength, etc.) that provide most of the existing features plus many new features for medical devices including optical power transmission, sensing, and communication. In addition, glass and plastic fiber optics are available commercially and have been widely utilized in communication and remote lighting application. The present invention arose driving investigation of fiber optic based sensors and devices including mechanisms for converting optical energy to usable acoustic or mechanical energy at the distal end (tip) of the optical fiber. During the investigation from which the present invention arose, the following technical problems were addressed:

1. Provide power (electrical, thermal, acoustic, optical, mechanical, etc.) at the distal tip of a small (250–500 micron) catheter or device.
2. Eliminate MRI incompatible materials (magnetic materials) from the medical device.
3. Reduce extraneous heating (at bends in wires, rotation induced fire hose effects, etc.).
4. Increase the communication bandwidth to the distal tip.

The features that address above items 2, 3, and 4 are due to the optical fiber itself. For instance: plastic and/or glass fibers do not interact with MRI fields (item 2) the way electrical conductors do (for instance, mini-coax cables, guidewires, etc.). When an optical fiber is bent to navigate through blood vessels, it does not produce heat like an electrical or ultrasonic conductor would (item 3). If optical energy is used to drive a mechanical device at the distal tip of the fiber, the optical energy transfer does not create a "fire hose" effect. This effect is seen in pressurized systems (e.g. flowing water, translating opposing wires, rotating wires). The information carrying capacity of an optical signal is fundamentally higher than an equivalent sized electrical conductor (item 4).

By providing modular energy conversion interfaces (photons to thermal or electrical or mechanical or acoustic), at the distal tip of an optic fiber, medical devices can be designed with greater utility and for less cost. One example is to create the "wall plug outlet" or universal terminal at the end of a fiberoptic by placing a photo-electric transducer there, whereby the electrical energy can then be used to perform electronic (communication, computing, etc.), mechanical (grip, release, biopsy, steer, rotate, etc.), and/or acoustic (ultrasonic imaging, listening, etc.) actions. A second example is to provide a comparable device that uses light-sensitive plastics, such as photo-thermal material, to directly control temperature—based shape memory actuated devices (polymers and/or alloys). A third example is to provide sensors (electronic, thermal, mechanical) that can be "stocked" at the tip of a fiberoptic cable and the information relayed back to the proximal end of the fiber optic using optical signatures or by modulating the light power, whereby the physical state of a catheter mounted microgripper, etc, as well as the environment involved (pH, temperature, glutamate, position, etc) can be readily communicated to a user. A fourth example is a device for actuating a catheter based microgripper and for determining that an object to be deposited had been released at the desired location. A fifth example, is the use of an electromechanical transducer or motor for actuating the microgripper, which is powered by discharge of a capacitor, and the capacitor is charged by conversion of light energy.

The above-referenced U.S. Pat. No. 6,102,917 is directed to a system for releasing a target material from an SMP microgripper located at the distal end of a catheter, wherein the SMP microgripper was activated by light energy via an optical fiber, and wherein the system includes a release sensing and feedback arrangement via fiber optics couplers, a photo detector, etc., While the present invention utilizes light via one or more fiber optics to deposit and sense release, etc., as in U.S. Pat. No. 6,102,917, in the present invention the light energy is converted to other forms of energy and thus the light energy does not merely function as an SMP activator and light sensor.

Referring now to the drawings, FIGS. 1A–1B, 2A–2B, 3 and 4 illustrate embodiments of prior art microgrippers which are mounted to a distal end (tip) of a catheter for depositing objects, such as an embolic coil, in a blood vessel, for example. FIG. 5 schematically illustrates an embodiment of the catheter-based medical device or system of the present invention, while FIGS. 6–9 schematically illustrate four general basic approaches for caring out the invention, and FIGS. 10 to 24 illustrate these basic approaches in greater detail.

Figure 1B:
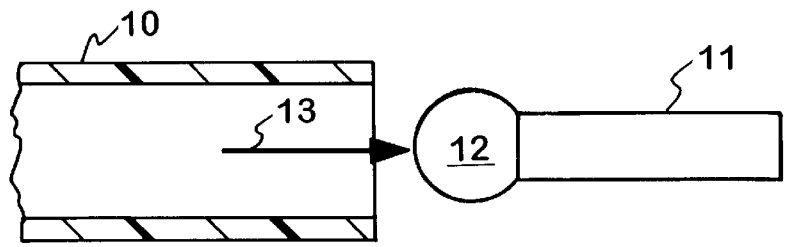

The microgripper embodiment of FIGS. 1A–1B comprises on shape memory polymer (SMP) tube 10 having one end connected to a catheter, not shown, and the opposite end retaining a material 11 to be deposited, such as an embolic coil having an enlarged end 12. The end 12 is retained in tube 10 by heating, applying pressure, and cooling the tube. As seen in FIG. 1B, the material 11 is released from the tube 10, as indicated by arrow 13, upon heating of the SMP tube above a predetermined transformation temperature whereby the tube returns to its original position thus releasing the enlarged end 12.

Figure 2A:
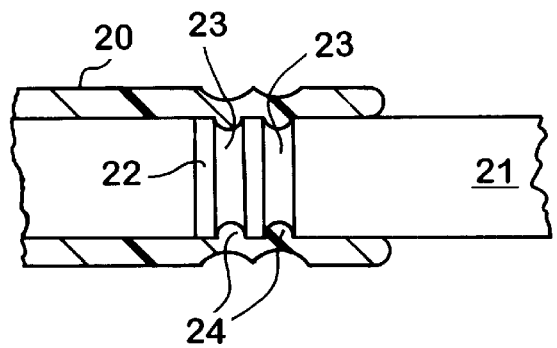
FIGS. 2A and 2B illustrate another prior art shape memory polymer microgripper for retaining and releasing a deposit material such as an embolic coil.
Figure 2B:
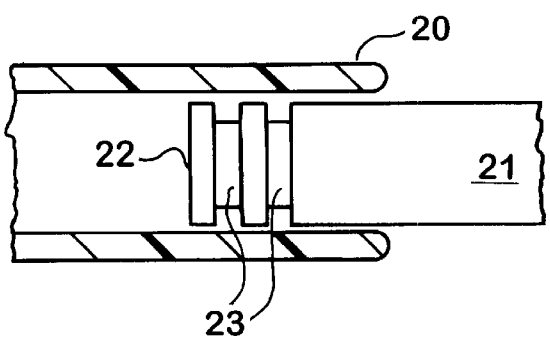

FIGS. 2A–2B illustrate another embodiment of an SMP tube or microgripper, but which utilized a deposit device having grooves at one end rather than an enlarged end as in FIGS. 1A–1B. In FIG. 2A the SMP tube 20 returns an object 21 to be released, as shown in FIG. 2B, the object 21 having an end 22 with grooves 23 therein, and upon heating, pressuring, and cooling the end of tube 20 the SMP material deforms to conform with the grooves 23 whereby portions 24 of the SMP tube extends into the grooves 23 and retains the object 21 therein. Upon reheating of the SMP tube 20 above a predetermined transformation temperature the tube 20 returns to its original shape thus releasing the object 21, as seen in FIG. 2B.

Figure 3:
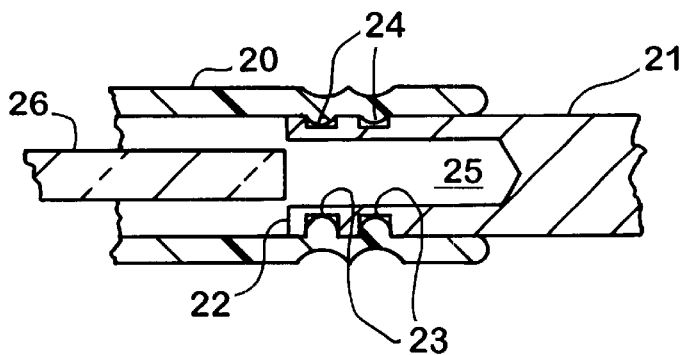
FIG. 3 illustrates a prior art microgripper similar to FIGS. 2A–2B but utilizing an optical fiber and a light trap for at least causing release of the deposit material.

FIG. 3 illustrated an SMP microgripper similar to FIG. 2A and corresponding components have similar reference numerals, but utilized light energy to heat the tube for releasing the object. Optical heating provides a more uniform and core efficient method to heat the SMP tube for releasing the object therefrom. In FIG. 3, an object, such as a coil, 21 is retained in a SMP tube 20 via grooves 23 in end 22 of object 21 and portions 24 of tube 20, as described above in FIG. 2A. The object 21 is modified to include a cavity forming a light trap 25, which functions to heat the SMP tubing 20 by directing light into the trap 25 by an optical fiber 26, which extends through an associated catheter, not shown, into the SMP tubing 20. Upon heating the SMP tubing to its transformation temperature, the tubing 20 returns or reverts to its original shape, releasing the end 22 of object 20, as in FIG. 2B as described above.

Figure 4:
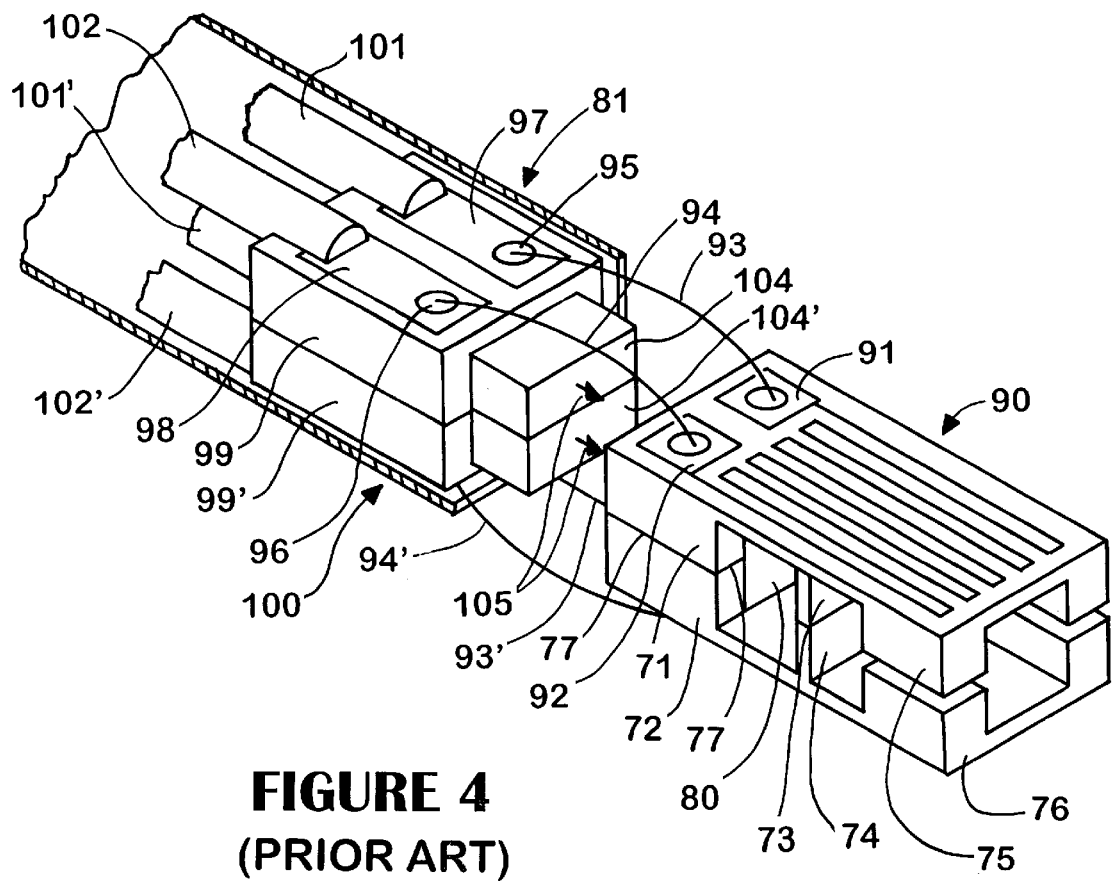
FIG. 4 illustrates another prior art microgripper, which utilizes shape memory alloy films and in situ resistive heaters to activate cantilever members of the microgripper.
Figure 5:
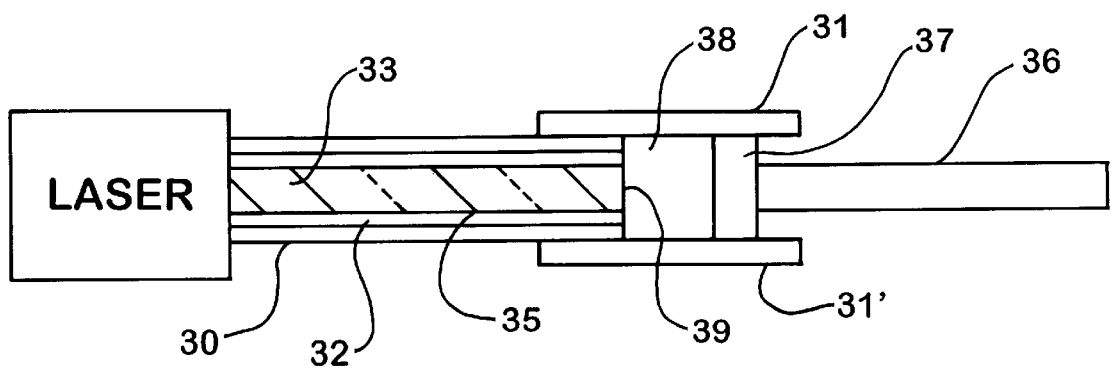
FIG. 5 schematically illustrates an embodiment of a medical device made in accordance with the invention.

FIG. 4 illustrates a microgripper similar to that of above reference U.S. Pat. No. 5,645,564, mounted to a distal end of a catheter and activated by shape memory alloy (SMA) films mounted on the cantilever members of the microgripper. As shown in FIG. 4, the device comprises a microgripper generally indicated: at 7, connected to a wiring jacket generally indicated at 81 located within a distal end of a catheter tube 85. The microgripper 70 comprises a pair of cantilevers 71 and 72 having separators 73 and 74 and teeth 75 and 76, with the cantilevers 71 and 72 having abutting ends bonded as together indicated at 77 which are mounted to a support member 80. The wiring jacket 81 is connected to the microgripper 70 via a SMA film resistive heater, generally indicated at 90, on cantilever 71 and having contact pads 91 and 92, which are connected via leads 93 and 94 to contact pads 95 and 96 on conductive films 97 and 98, such as copper, bonded to polymide member 99 of electrical feedthrough ribbon, generally indicated at 100 as indicated by leads 93' and 94', and identical resistive heater and electrical connection arrangement is provided between cantilever 72 of microgripper 70 and the conductive film on polymide member 99' of wiring jacket 81. The polymide members 99 and 99' and associated copper films are connected to insulated feedthrough wire 101/102 and 101'/102' of ribbon 100, and are located within a catheter tube 103. The polymide members 99 and 99' include protruding end sections 104 and 104' which, as indicated by the arrows 105, extend into the hollow channel 80 of microgripper 70. The wiring jacket 81 is secured to microgripper 70 by a heat shrink tube 106.

FIG. 5 illustrates an embodiment of a micromechanical system for medical procedures which incorporates the invention into a catheter having a distal end for insertion into and manipulation within a body and a proximal end for a user to control the manipulation of the distal end. As shown in FIG. 5, a space between a distal end of a fiberoptic cable disposed within the catheters and an end of an embolic coil (deposit material) defines a chamber within which a laser-light-to mechanical-power converter is located to receive laser light from the fiberoptic cable and convert it to energy for actuating the microgripper composed of SMP tubing, as schematically illustrated in FIGS. 6–8. Also within this chamber is located sensors of various types, as schematically illustrated in FIGS. 6–8. The embodiment of FIG. 5 comprises a catheter 30 having a SMP tubing 31 mounted to a distal end 32 and an optical fiber or fiberoptic cable 33 (containing a number of optical fibers disposed therein which is positioned to transmit light energy from a laser 34 mounted at the proximal end of the catheter 30. Note that the fiberoptic cable 33 has a distal end 35 proximate to the distal end 32 of catheter 30. A deposit material or embolic coil 36 has an enlarged end 37 retained in an outer end 31' of SMP tubing 31, such as shown in FIGS. 1A, 2A and 3, and the end 37 of coil 36 is located in a spaced relation to the distal ends of the catheter 30 and fiberoptic cable 33 to define a chamber 38. Chamber 38 may function as a light trap, as in FIG. 3, to heat the SMP tubing 33 to release the end 37 of coil 36 and as a location for a laser-light-to-mechanical-power converter indicated generally at 39, such as a photo-electric transducer of FIG. 6 or 8, or a light sensitive or photo-thermal material of FIG. 7. FIG. 6 illustrates a "wall plug outlet" at a distal end of the optical fiber or fiberoptic cable 33', such as shown in FIG. 5, with the device 39 of FIG. 5 comprising a photo-electric transducer 40 located in the chamber 38' actuated by light from laser 34 along with an electrically actuator device, processor, or sensor, generally indicated at 41, the deposit material (embolic coil) being omitted. Thus, the electrical energy produced by the photo-electric transducer 40 can then be used to perform electronic (communication, computing, etc.), mechanical (grip, release, biopsy, steer, rotate, etc.), and/or acoustic (ultrasonic imaging, listening, etc.) actions of the device or devices indicated at 41.

FIG. 7 illustrates a device using light-sensitive material such as photo-thermal material 50 located in chamber 38' to directly control temperature-based shape memory devices (polymers and/or alloys), or mechanical device 51, such as illustrated in FIGS. 1A–4. The preferred arrangement is to dope the material with light absorbers to localized heating and possible coat with material as well to manage heating. Materials that expand can be activated by fiber arrays to control position.

The ability to use lasers to probe the environment within a body is useful by itself, but also as a means of determining the physical state of the actuated device. Several sensors can be "stacked" at the tip or distal end of optical fiber 33 of FIG. 5, as generally indicated at 39, and illustrated schematically in FIG. 8. The information is relayed back to the proximal end of the optical fiber using optical signatures or by modulating the light power. The combination of light-sensitive or photo-thermal materials and temperature sensors will greatly increase the information of the physical state. Electrical energy can be used to power electrochemical sensors or bridge circuits for impedance measurements and to communicate results back down the fiber optic or fiber optic bundle or cable. FIG. 8 schematically illustrates a photo-electric transducer 60 to actuate a sensor 61 and an actuator 62 via electrical energy produced by the photo-electric transducer 60. The sensors 61 maybe designed to sense ph, temperature, glutamate, position, etc.

The laser light via the optical fiber of FIG. 5 can be use to discern when the embolic coil or deposit material is released from the microgripper. The same light that is used to power the device and/or probe the environment via various sensors, as shown in FIG. 8, can determine when the embolic material is released, by monitoring the reflected light which changes as the gap between the distal end of the optical fiber and the embolic material widens (the chamber 38 in FIG. 5 would lengthen). Such a monitoring system is shown in FIG. 9A which includes a probe source 64, which may be the laser 34 of FIG. 5, reflectors 65 and 66 which reflect light indicated at 67 from chamber 38' back to probe source 64. The reflected intensity decreases as the gap width increases as shown in FIG. 9B.

FIGS. 10–14 illustrate energy conversion interfaces in accordance with the present invention for miniaturized systems which utilize electrically as the energy input, and involves a photo-voltaic cell to convert optical energy to electrical energy thereby resolving the above discussed technical problems relative to providing power at the distal tip, elimination of MRI incompatible materials, reduction of extraneous heating, and increasing the communication bandwidth to the distal tip.

Figure 10:
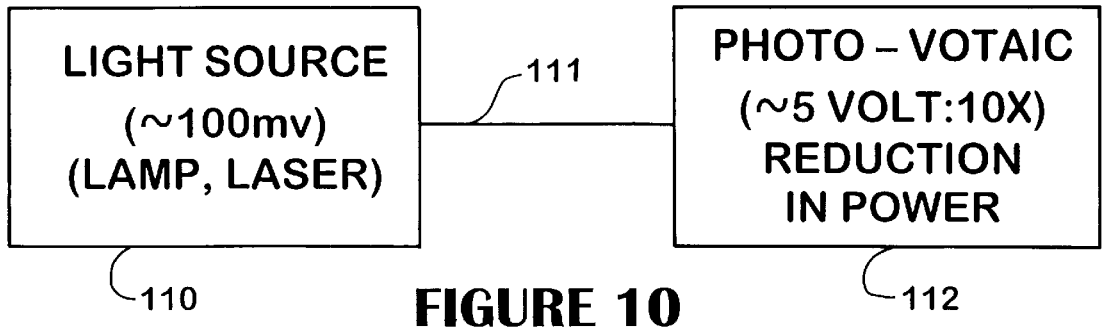
FIG. 10 illustrate an embodiment comprising a light source, fiber optic and photo-voltaic section.

FIG. 10 illustrates the basic concept of an energy conversion interface utilizing a photo-voltaic cell located at the distal end of a fiber optic which is connected at is proximal end to a light source. As shown, a light source indicated at 110 which for example may be a 100 mW source produced by a lamp or laser is connected to a fiber optic 111 connected to power a device via a photo-voltaic cell 112, which for example may be ~5 Volt, a 10 times reduction in power.

Figure 11A:
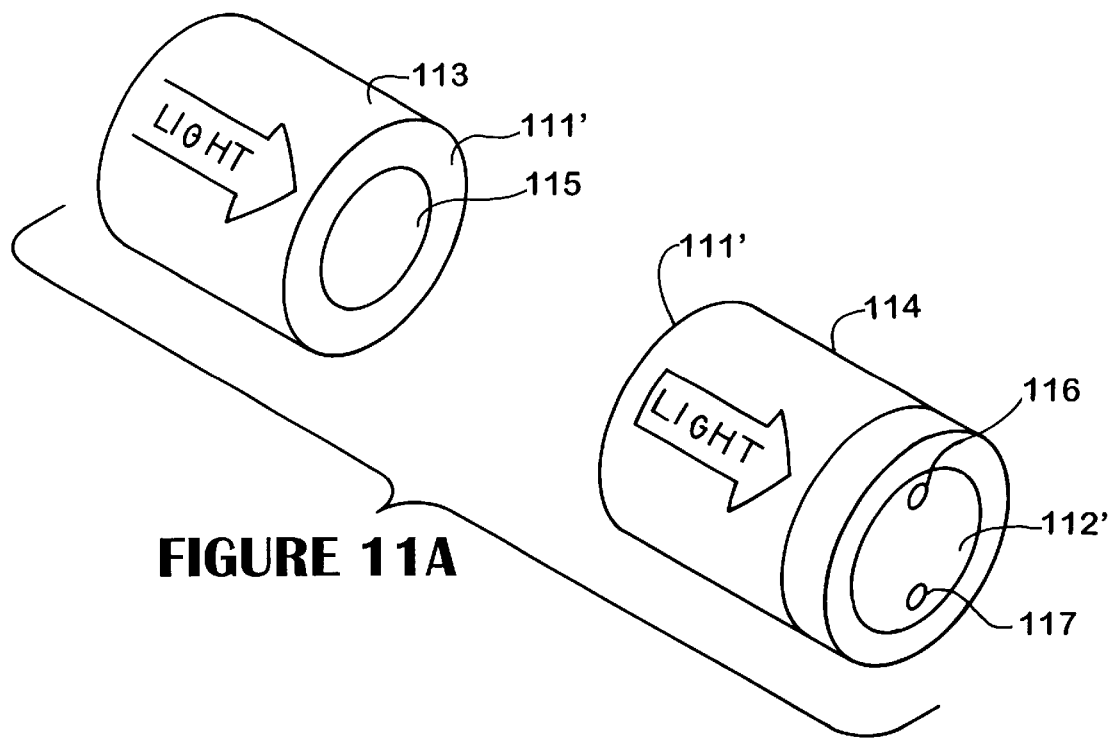
FIG. 11A illustrates fiber optic sections an a photo-voltaic section for the embodiment of FIG. 10.
Figure 11B:
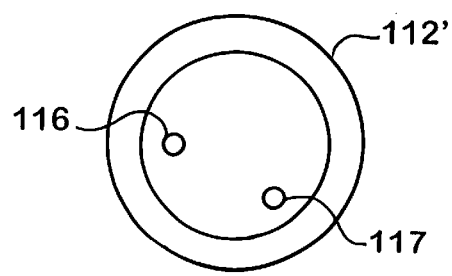
FIG. 11B is an end view of the photo-voltaic section of FIG. 11A.

FIGS. 11A and 11B illustrate an embodiment of a fiber optic with a photo-voltaic cell mounted at the distal end of the fiber. As shown, the fiber optic generally indicated at 111' is shown in two sections 113 and 114 with each section including a core or hollow 115 through which light, indicated by legends pass, and with section 114 being mounted to a photo-voltaic cell or member 112' having electrical leads, or contact pads 116 and 117, which as shown in FIG. 1B function as ground and Vcc leads, respectively.

From electrical energy, the power can be converted into a variety of modes including thermal e.g., using a resistive heating element, as seen in FIGS. 12A and 12B. A resistive heater is illustrated in FIG. 12A at 118 which may comprises a resistive electrical element 119 having contact pads 120 and 121 embedded in a shape memory polymer (SMP) member 122, or while not shown, be formed on top of a shape memory alloy (SMA). The resistive heater 118 is mounted adjacent the photo-voltaic cell 112' as shown in FIG. 12B to be powered, by the cell 112', whereby electrical leads or contact pads 116 and 117 of cell 112' are in contact with contact pads 120 and 121 of heater 118.

The electrical contacts can be made of a variety of ways including "S" and bump pads that make contact upon physical connection of the adjacent members or layers (photo-voltaic cell 112' and resistive heater 118). The separate modules (resistive heater 118, photo-voltaic cell 112' and fiber optic section 114 as shown in FIG. 12B) can be joined using cements, epoxies, etc. There are a variety of alignment systems available from the fiber optic industry to facilitate this assembly.

In order to make the connections simpler; it may be appropriate to use a different geometry electrical contacts. For instance, concentric circular electrodes would reduce alignment complexity (rotation of adjacent modules would no longer matter). FIG. 13 illustrates a photo-voltaic cell, generally indicated at 125 having concentric ground 126 and Vcc 127 electrodes mounted in a substrate 128.

It is also possible to leave a small window (or use a laser wavelength that transmits through the substrates) to facilitate alignment of the modules using light propagated down the fiber and measured at the distal tip.

The electrical energy produced by the photo-voltaic cell is used to power a device, such as may be mounted at the distal end of a catheter, as shown in FIGS. 6–8. This has valve for an/off type system (e.g. mechanical release, agitation, etc.). The value of a modular electrical source at the distal end of an optical fiber is significantly increased if data can be communicated back from the distal tip to the proximal end for evaluation by the user/physician, as schematically illustrated in FIGS. 9A and 9B. The electrical power produced by the photo-voltaic cell can also be used to energize digital circuits (e.g. microprocessor, CCDs and other sensors). The value of a microprocessor at the tip depends on the intended use and for many sensors, the value of being at the distal tip is significant. It could eliminate or reduce the need to aspirate or biopsy fluids and tissue samples. There are ways to modulate the optical power. However, since a single optical fiber for communication could have a core diameter the on an order of a few to tens of microns in diameter (about 10 to about 50 microns), there are opportunities and advantages to isolate optical communications from optical power. A very similar approach exists combining them as it applies to a light lock/key is disclosed in U.S. Pat. No. 6,055,079 issued Apr. 25, 2000 to K. G. Hagans et al, assigned to the same assignee. By way of example, one could pick a 50 micron fiber for the cases where power had to be transmitted via the fiber and a 9 micron fiber for communication back from the surgical location. One would also consider a 125 micron cladding diameter. The cladding is not the buffer layer of the fiber optic but an integral part of the fiber needed to make the fiber optic transmit light. The cladding portion of the fiber could be 85 microns in diameter but not much thinner. If the core diameter goes to a few microns for the fibers that transmit the power one would have trouble transmitting enough power to the surgical location without exceeding the power density capability of the fiber and damaging it. The size of the communication fiber could also be smaller but is limited by the cladding diameter as well. Nine micron core fiber is a standard 1300 nm single made fiber size and commonly available.

With both electrical power and a communication circuit available, it is possible to place a variety of sensors at the distal tip of the fiber optic. The modular concept of the power supply should be applied to provide communication connectors through the different modules and back to the proximal end of the fiber. This can be done as an array of fibers where separate functions can be devoted to individual fibers (e.g. power, com-line 1 for electrochemical sensor, com-line 2 for CCD output, com-line 3 for temperature sensor, com-line 4 for ph sensor, etc.). The power fiber must attach to an interface that distributes electricity to the other fibers.

FIGS. 14A and 14B partially illustrate an embodiment similar to FIG. 11A but with a bridge electrical element or module which measures electrical impedance of the exposed distal tip and transmits this signal back to the user. As shown in FIG. 14A, the bridge module generally indicated at 130 includes a substrate 131 an air of electrical contact pads 132 and 133 interconnected by leads 134 and 135, and a pair of electrical contact pads 136 and 137. As seen in FIG. 14B the bridge module 130 is positioned adjacent a photo-voltaic cell or module 112' mounted to an optical fiber section 114, as in FIG. 11A, such that contact pads 132 and 133 are in electrical contact with electrical leads or contact pads 116 and 117 of photo-voltaic cell 112'. Contact pads 136 and 137 are electrically connected to an impedance sensor 138 that directs a signal back to the user as indicated by arrow 139.

Because optical fiber dimensions are millimeter and smaller, the sensors and interfaces would need to be microfabricated and connected using known lithographic techniques, and microfabricated electrochemical sensors, for example, have been developed at the Lawrence Livermore National Laboratory. It should be recognized that the embodiments of FIGS. 10–14 are not to size and the attached modules (power supply, sensor, bridge element, etc.) would be larger in diameter than the optical fiber or array of fibers, and still yields all the benefits (item 2–4 above) of using fibers.

Figure 15A:
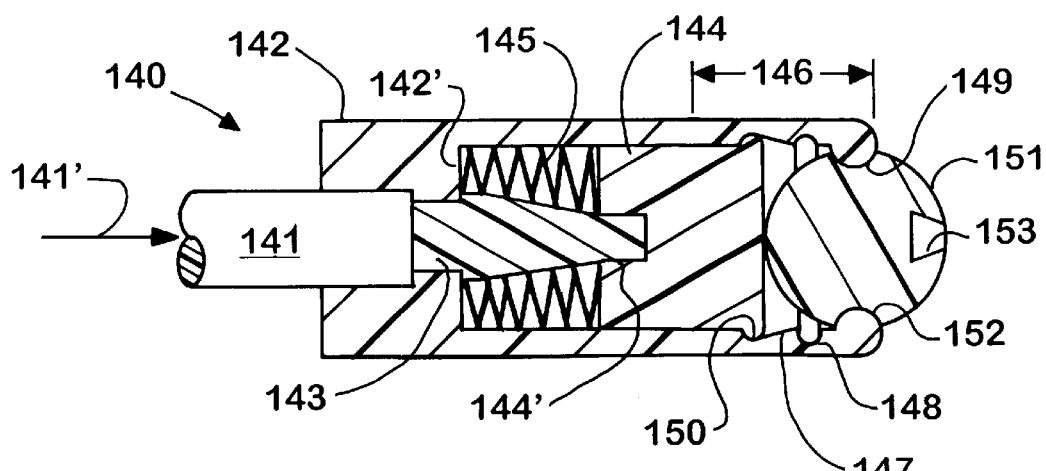
FIGS. 15A and 15B are schematic partial cross-sectional views of an embodiment of an optically activated catheter for depositing a device.
Figure 15B:
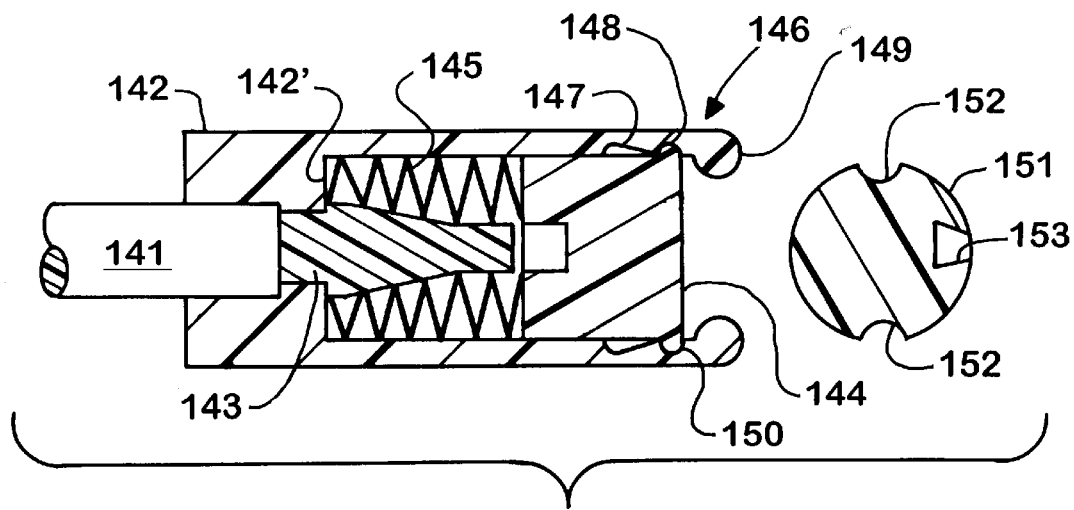
Figure 16A:
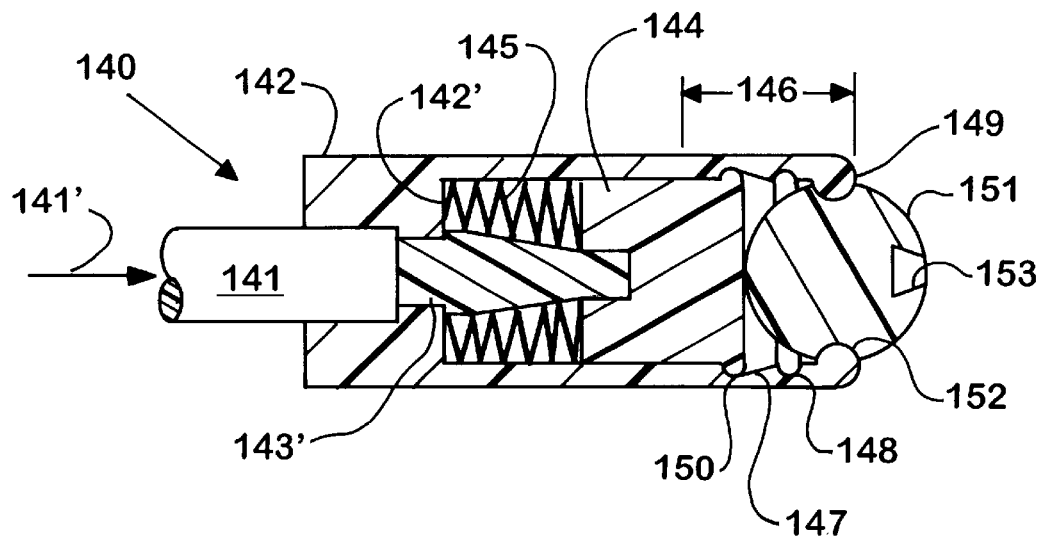
FIGS. 16A and 16B illustrate an embodiment similar to FIGS. 15A and 15B except that upon optical heating the ultraviolet sensitive plastic member disintegrates.
Figure 16B:
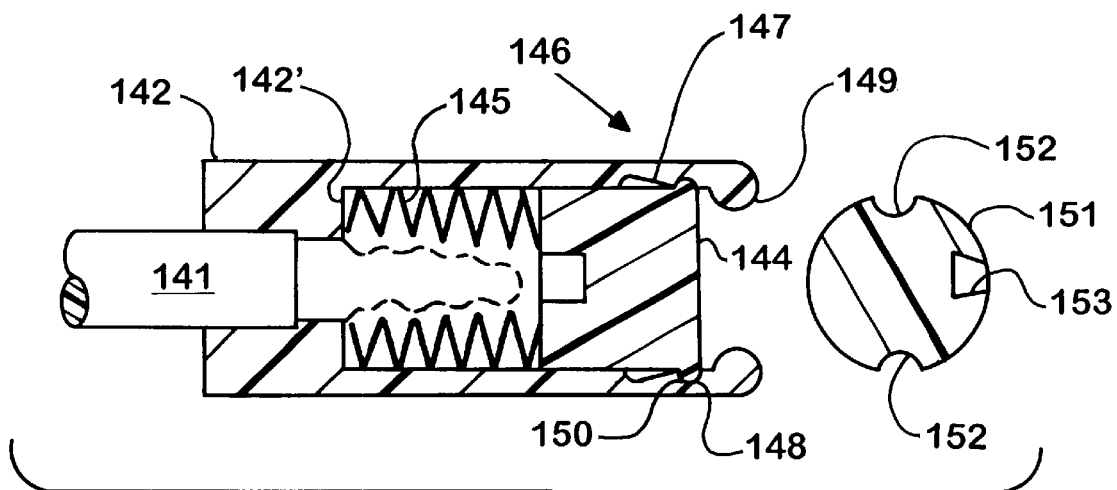

FIG. 7 schematically illustrates a photo-thermal arrangement involving a fiber optic, a quantity of photo-thermal material, and a mechanical device activated by the photo-thermal material when heated by light via the fiber optic. FIGS. 15A and 15B illustrate in partial cross-section an embodiment for carrying out the basic approach of FIG. 7. As seen in FIG. 15A, a device generally indicated at 140, which for example may be mounted to distal end of a catheter, and comprises an optical fiber 141 connected to receive ultra violet laser light indicated at 141', and connected at one end to a hollow plastic body or member 142 within which are located an ultraviolet sensitive plastic member 143, a plastic piston 144, and a compressed cushion (spring) 145 extending around member 143 and intermediate plastic piston 144 and a flange section 142' of plastic body 142. Member 143 is secured to piston 144 as by gluing, etc. indicated at 144'. Body or member 142 includes a distal end or slit zone 146 having tapering section 147, a groove 148 and an inwardly protruding section 149. As seen in FIG. 15A, the piston 144 includes a protruding end section 150, which to located at the larger (left) end of the tapering section 147 of body 142. Piston 144 abuts a plastic ball 151 having a centrally located groove 152 and an anchor hole 153. The inwardly protruding section 149 of body 142 is located in groove 152 of ball 151, and the anchor hole 153 is adopted to retain a device, such as an embolic coil, as shown in FIG. 5, to be inserted in a blood vessel, for example. Upon actuation of the device of FIG. 15A by laser light 141' via optical fiber 141, the ultraviolet sensitive member 143 is heated causing glued section 144 to melt, allowing expansion of compressed cushion 145, causing movement of the piston 144 along tapering section 147 of body 142 which expands the slit zone 146 causing withdrawal of protruding section 149 from groove 152 in ball 151 allowing release of the ball 152 from device 140, as seen in FIG. 15B. Movement of piston 144 is terminated by protruding section 150 entering groove 148 in the slit zone 146 body 142, as seen in FIG. 15B. Thus, a photo-thermal material is activated by light energy via a fiber optic to actuate a mechanical retaining device. Thus, light-energy is converted into mechanical energy. The The embodiment of FIGS. 16A–16B is similar to that of FIGS. 15A–15B except that upon being heated the ultraviolet sensitive plastic member disintegrates an UV deterioration approach. Corresponding components to those of FIGS. 15A–15B are given corresponding reference numerals. As shown in FIG. 16B, when the ultraviolet sensitive plastic member 143' of FIG. 16A is heated by light energy 141' via optical fiber 141, member 143' disintegrates at a temperature in the range of 40° to 80° C., for example, whereby compressed cushion 145 expands against piston 144 as described above relative to FIG. 15B, causing release of ball 151. The FIGS. 16A–16B approach is a "one-shot" arrangement, requiring the replacement of the ultraviolet sensitive plastic member 143' after each activation.

Figure 17:
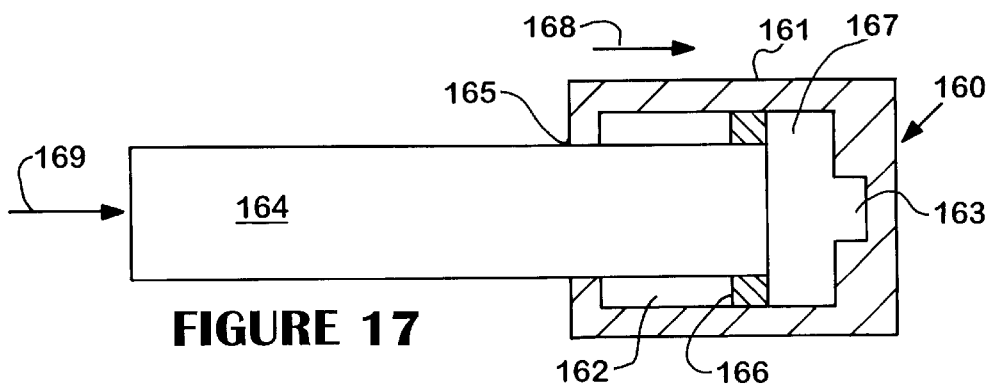
FIG. 17 is a cross-sectional view of a light activated fluid actuated device.

In the embodiment of FIG. 17, light is used to drive a fluid actuated device wherein heated fluid causes movement of a slider or moveable member. As shown, the device generally indicated at 160 comprises a slider 161 having a chamber of a larger cross-section 162 and a smaller cross-section 163, an optical fiber 164 extends through an opening 165 into chamber section 163 and is secured to a stop or member 166. The chamber section 163 and a portion of chamber section 162 contains a working fluid 167. Light, such as laser light, indicated by arrow 169 is directed through fiber 164 and creates bubbles in the working fluid 167 at a temperature in the range of 40° to 100° C., for example causing the working fluid 167 to expand which causes slider 161 to move to the right as indicated by arrow 168, and subsequent bubbles caused heating of the fluid 167 via light 168 through fiber 164 creates a pressure wave which transmits through the fluid 167 causing the slider to move in the direction of arrow 168 until it bottoms out against stop 166. Thus, light energy is converted into mechanical movement via a working fluid.

Figure 18:
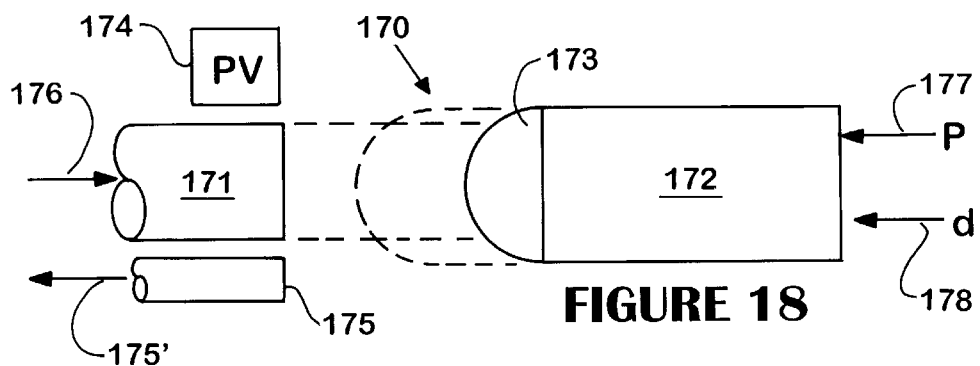
FIG. 18 illustrates an embodiment of a light-to-mechanical sensor for measuring distance or pressure by reflected light intensity.

FIG. 18 illustrates an embodiment of a conversion device involves light-to-mechanical sensor for indicating a change in either distance or pressure utilizing a reflected light intensity approach. The sensor generally indicated at 170 basically comprises an optical fiber 171 movable member or a device 172 to be moved (deposited) having a curved mirror end surface 173, a photo-voltaic (PV) cell 174 and a return fiber optic 175. When a laser light pulse 176 is directed through optical fiber 171 light is reflected from mirror surface 173 onto the PV cell 174 for conversion to an electrical signal, and into the fiber optic 175 for direct reflection as indicated by arrow 175' down the fiber 175 to an external control device. As device 172 is moved from its original position, shown in dash line, to it position, shown in solid lines, by a mechanism not shown, both the pressure (P) indicated by arrows 177 and the distance (d) indicated by arrow 178 changes and the intensity of the light reflected from mirror surface 173 onto PV cell 174 and into fiber optic 175 changes. Knowing the distance (d) as a function of time, then velocity and acceleration can be determined. The device or movable member 172 may be moved by any of the mechanisms described above activated by any of photo-voltaic energy, fluid energy or mechanical energy. If desired, either the PV cell 174 or the return fiber optic 175 may be omitted. Also, a single optical fiber can provide pulse and transmit reflection to provide spacing change and therefore distance of pressure. This would use a flat surface with an "interference" pattern on it.

The embodiment of FIG. 18 can be modified to position a laser diode (LD) in alignment with the PV 174 and form the PV so as to be composed of a plurality of stacked unit (a PV array), which provides an electrical approach based on photo voltaics where the number of photo cells illuminated is translated into a voltage sent out via the laser diode. Since size is an issue, even assuming 25×200μ photocells, current for the VCSEL is marginal (because of the reflected power) and the number of photo cells limit the resolution. The fiber optic 171 may be a fiber bundle of 10μ/25μ OD fiber drawn to an imaging bundle. The fiber bundle could a configuration with a central fiber of 10μ surrounded by rows of fibers with a cross-section of 250μ. Size of reflection on the imaging bundle determines pressure.

Figure 19A:
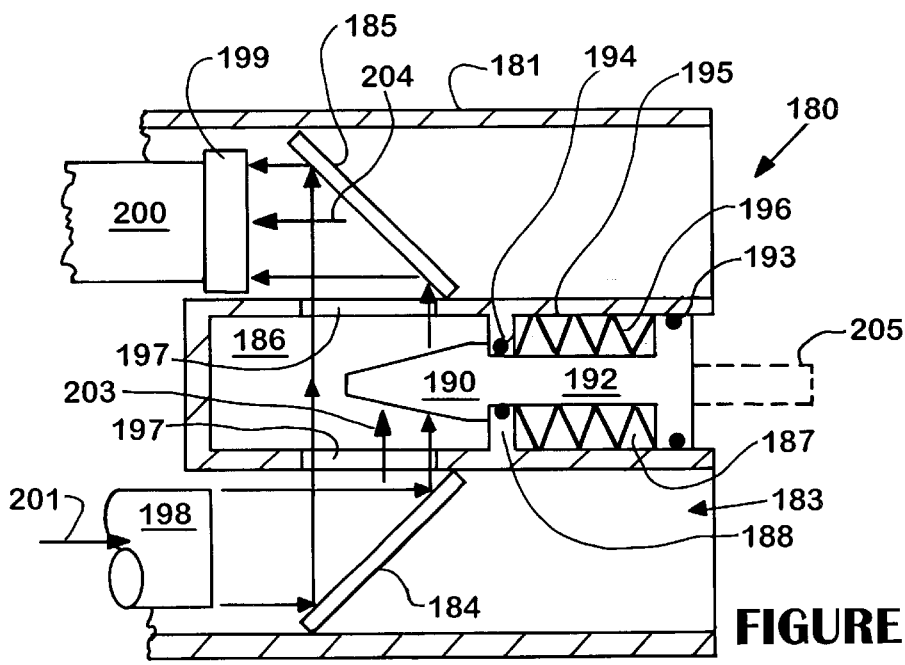
FIGS. 19A and 19B illustrate another embodiment of a light-to-mechanical sensor, with FIG. 19A being a top view and FIG. 19B being a partial side view.
Figure 19B:
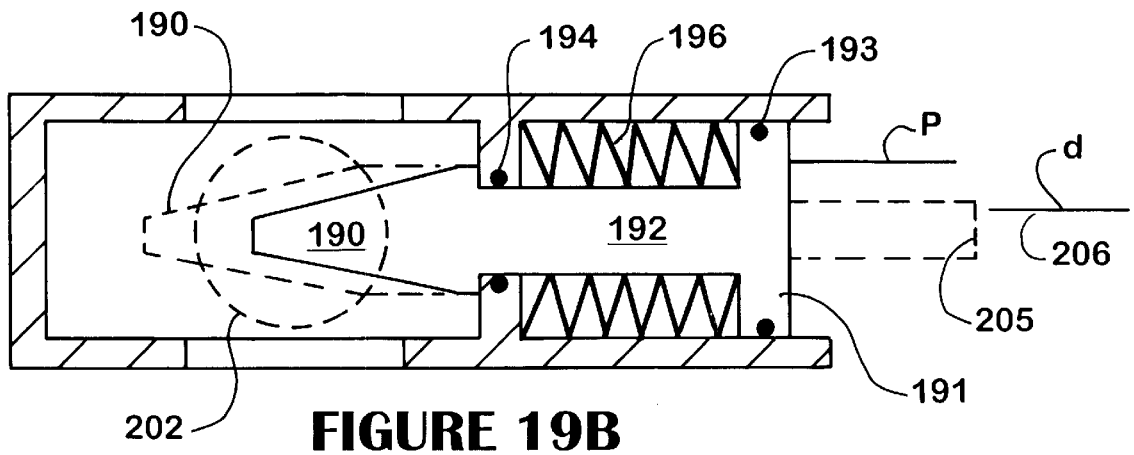

FIGS. 19A and 19B illustrate another embodiment of a light-to-mechanical sensor for determining change in distance or pressure by change in the light beam. As shown, the sensor generally indicated at 180 comprises and outer housing or body 181 defining a chamber 182 and within which is located a central body or housing 183 and a pair of tilted mirrors or reflectors 184 and 185, with central body 183 including a pair of chambers 186 and 187 formed by a cross member 188, and 187 in which a movable member 189 is located. Moveable member 189, which may constitute a graded neutral density (ND) filter, includes a head portion 190, and a piston portion 191 interconnected by a shaft portion 192, with a seal (o-ring) 193 located around the periphery of piston portion 191 and a seal (o-ring) 194 mounted around an opening 195 in cross member 188 and extends around shaft portion 192. A spring 196 is located in chamber 187 around shaft portion 192 and intermediate cross-member 188 and piston portion 191 of movable member 189. Central body 183 is provided with a number of openings 197 in the area of head portion 190 of movable member 189. Mounted intermediate outer housing 181 and central body 183 is an optical fiber or fiber bundle 198, a photo-voltaic (PV) cell 199 and optionally, or in addition to, a return fiber optic or fiber bundle 200.

Upon introduction of a laser pulse as indicated by arrow 201 through optical fiber 198, light beam, having a diameter indicated at 202 in FIG. 19B, is reflected by mirror 184 through an opening 197, passing head portion 190 of movable member 189, as indicated by arrow 203, and through another opening 197 onto mirror 185, which reflects the light onto PV cell 199 and/or into optical fiber 200, as indicated by arrow 204. As the head portion 190 of movable member 189 moves from its solid line position to a dash line position, as shown in FIG. 19B, or visa-versa, a greater or lesser portion of beam 202 is directed onto mirror, and the intensity of the light passing between mirrors 184 to 185 via openings 197 changes, thus registering and electrical output change at PV cell 199 and/or the amount of light-reflected through optical fiber 200. The movable member 189 is movable over a distance (d) indicated by dashed lines 205 and arrow 206, with the movement is caused by an actuator, not shown. Also, an actuator or other source of pressure (P) may be applied to the piston portion 191 of movable member 189, as indicated by the arrows 207 in FIG. 19B, which compressed spring 196, causing head portion 190 to move to the dash line position thereby blocking a greater amount of light between mirror 184 and 185. Thus, any movement of head portion 190 produces a change in the output of PV cell 199 or the volume (or intensity) of light passing into optical fiber 200.

Figure 20:
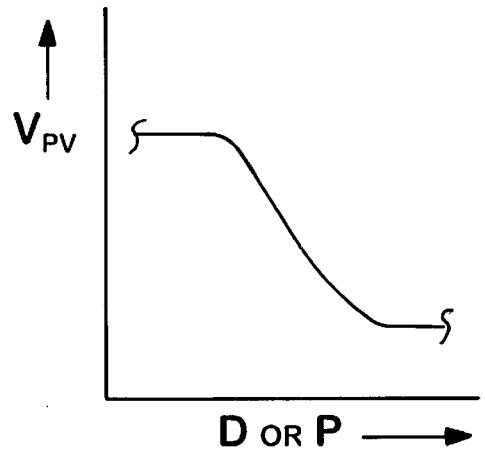
FIG. 20 graphically illustrates voltage vs distance or pressure for determining the velocity or acceleration of the movement of the device of FIG. 19B.

FIG. 20 graphically illustrates the change in the voltage, (Vpv) of the PV cell 199 as the distance of movement of movable member 189 or pressure applied against member 189 of FIGS. 19A–19B increases. Knowing distance as a function of time, then velocity and acceleration can be determined.

Figure 21A:
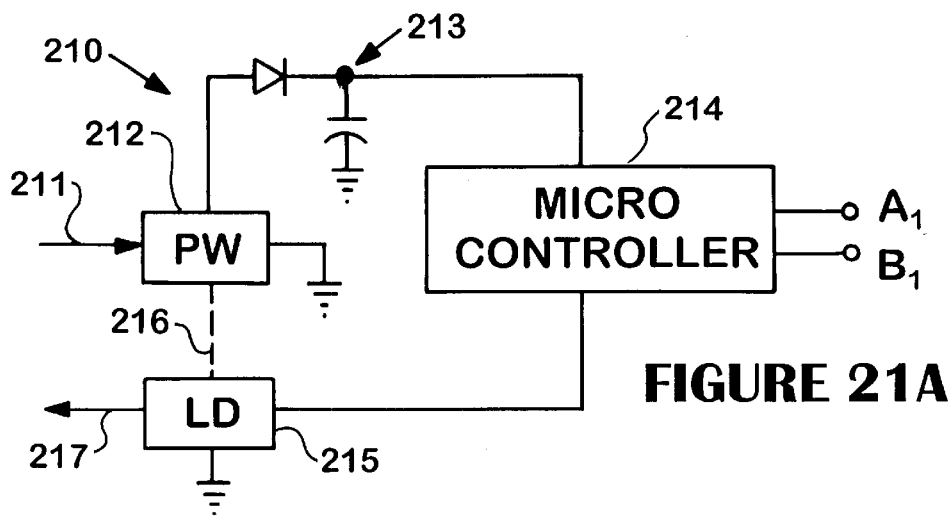
FIG. 21A schematically illustrates a light-to-electrical sensor, which utilizes a microcontroller, and wherein temperature and distance or pressure is considered, with temperature being illustrated in FIG. 21B, and pressure or distance being shown in FIG. 21C.
Figure 21B:
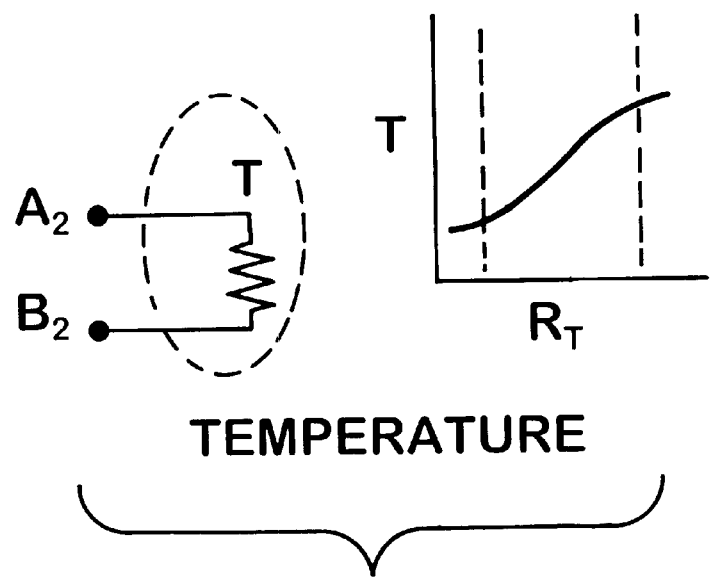
Figure 21C:
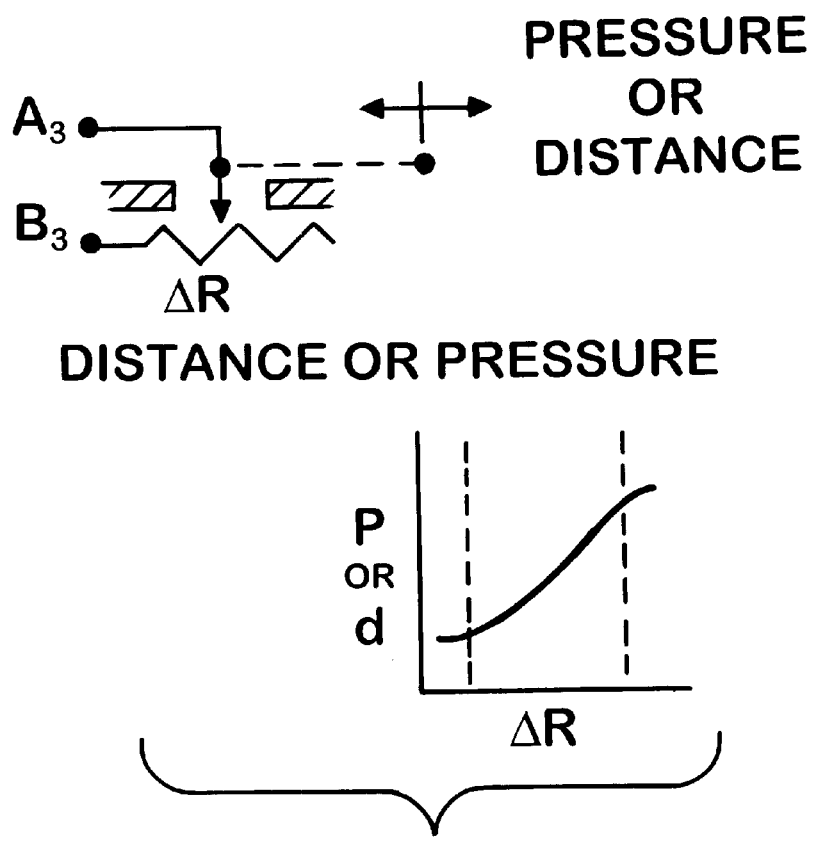

FIGS. 21A, 21B and 21C schematically or graphically illustrate a light-to-electrical sensor for temperature (FIG. 21B) and distance or pressure (FIG. 21C). Basically the embodiment of FIG. 21A generally indicated at 210 comprises a laser light indicated by arrow 211 directed onto a photo-voltaic (PV) cell 212, the output of passes via electronic circuitry 213 into a microcontroller or conditioning electronic unit 214, which is connected to a laser diode (LD) unit 215. The laser light from PV cell 212 is directed to LD unit 215 as indicated by arrow 216 where the laser light is directed back to a point of use, as indicated by arrow 217. Microcontroller 214 includes a pair of leads A, and B, which may be connected to leads $A_2$ and $B_2$ of a temperature sensor illustrated in FIG. 21B or connected to leads $A_3$ and $B_3$ of a or distance sensor illustrated in FIG. 21C. As pointed out above, knowing distance as a function of time, then velocity and acceleration can be determined.

Figure 22:
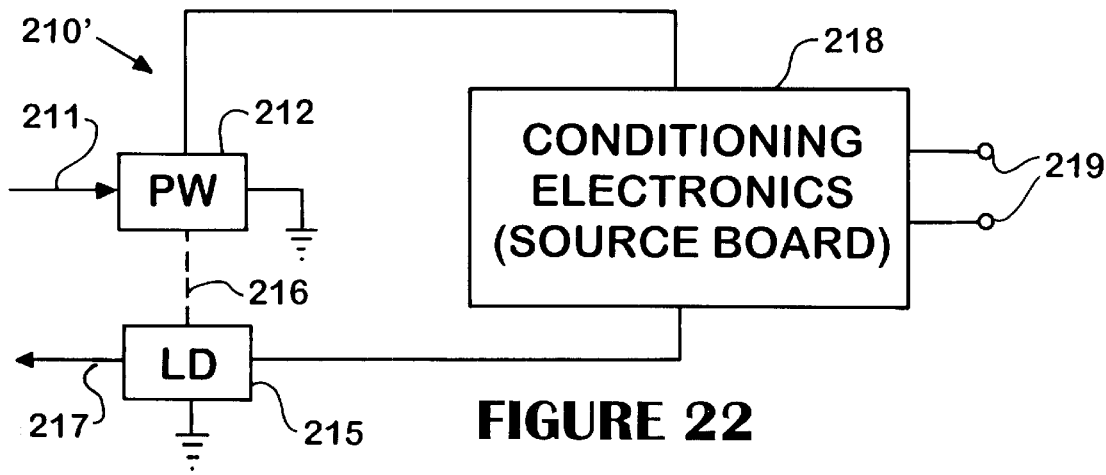
FIG. 22 schematically illustrates a light-to-electrical sensor arrangement which uses a "source board", "action terminal" or conditioning electronics, to connect and operate a variety of electrical devices, such as sensors.

FIG. 22 illustrates an embodiment of a light-to-electrical sensor similar to that of FIG. 21A except that he circuitry between the PV cell and microcontroller of FIG. 21A has been omitted a source board or conditioning electronics unit is utilized in place of the microcontroller. Components similar to those of FIG. 21A are given. Electrical energy produced by PV cell 212 directed into a source board (conditioning electronics unit) 218 with the output thereof connected to LD unit 215. Leads 219 of source board 218 connected to operate a variety of electrical devices, such as sensors.

The optic fiber bundle may consist of a fused $100\mu/125\mu$ coaxial fiber, a $50\mu/125\mu$ coaxial fiber or a $50\mu/125\mu$ (annular or square) side-by-side (custom) fiber; and the PV may be 2V (2 cell AaAs compound device) capable of 5 mA of peak current. The laser diode (LD) may be a 9 VC SEL vertical side emitting type optimized for a 10 w threshold current. The PV and LD can be packaged on a single surface with a left off technique to form an electro-optical chip. The signal conditioning electronics can be integrated behind the electro-optic ship, wherein the PV fiber is $100\mu$ and the LD fiber is 50 $\mu$m, for example.

Figure 23:
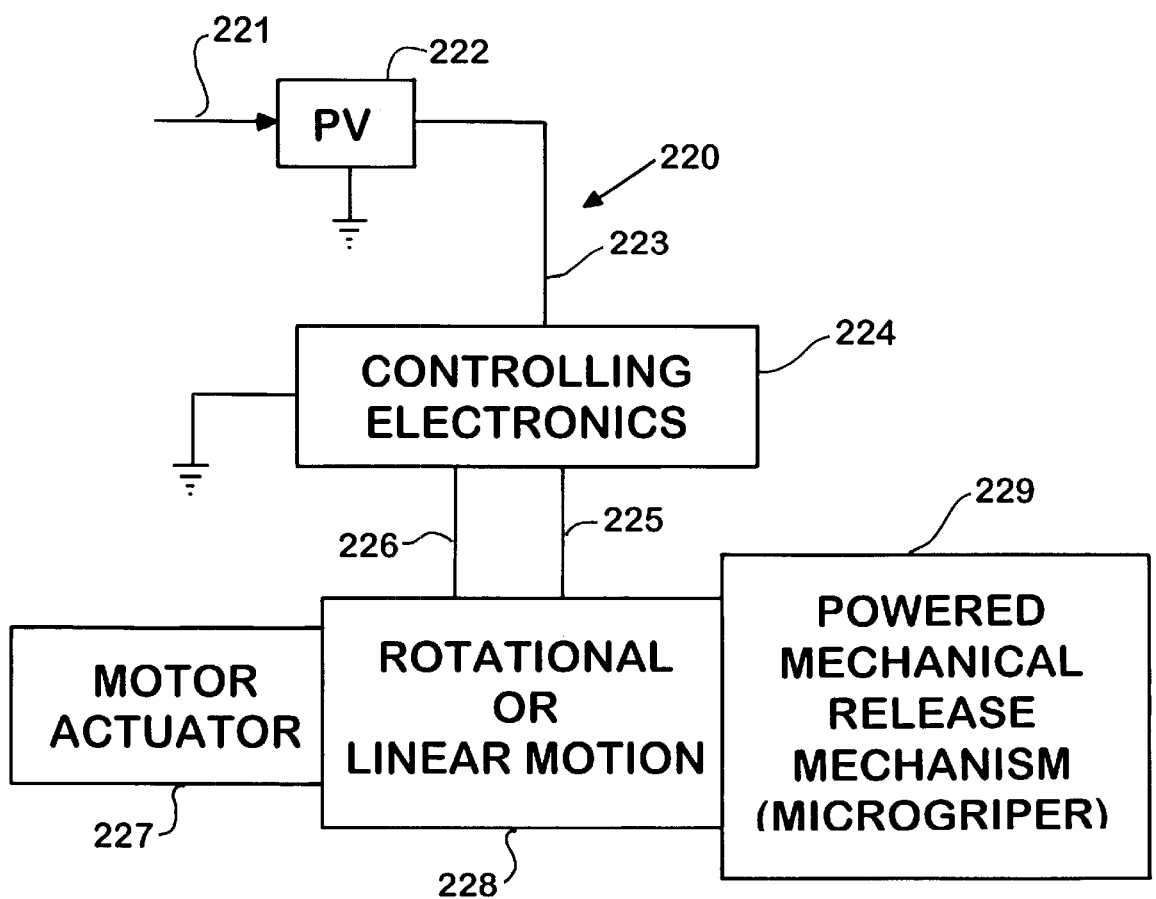
FIG. 23 schematically illustrates a light-to-electrical motor/actuator arrangement.

FIG. 23 schematically illustrates a light-to-electrical motor/actuator. Currently, the smallest traditional rotary commercial motor is produced Smoovy Company which is of a 3 mm diameter and a length of about 10 mm, and thus is large for micromotor or microactuator applications. A smaller linear stepper motor, ~1 mm diameter and ~7.5 mm long are being developed at the Department of Electrical Engineering, University of Minn. Also see U.S. Pat. No. 5,629,577 issued May 13, 1997 to D. L. Polla et al, entitled "Miniature Linear Motion Actuator". Thus, motors/actuators of a size small enough for microsurgical procedures are available, and the embodiment of FIG. 23 utilizes such a motor/actuator driven by conversion of light energy to electrical energy via a, PV cell and the motor/actuator converts the electrical energy into mechanical energy for actuation of release mechanisms, such as microgripper. By driving a rotary motor via a light-to-electrical conversion, according to the present invention, enables a rotary motor to drive a pump within the human body, for example. A 1000V photocell $\cong 100\mu \times 100\mu$ cell slices gives roughly a 1 mm square device.

As shown in FIG. 23, the light-to-electrical motor/actuator indicated generally at 220 comprise as light input indicated at 221 from a light source, such as a laser, directed via one or more optical fibers as described above into a PV cell 222 wherein light energy is converted to electrical energy which is transmitted via a lead 223 to a controlling electronics unit 224 having electrical leads 225 and 226 connected to a motor/actuator 227 which converts electrical energy into either rotational or linear motion (mechanical energy) as indicated by arrow 228 for driven a powered mechanical release mechanism 229, such as a microgripper.

Figure 24:
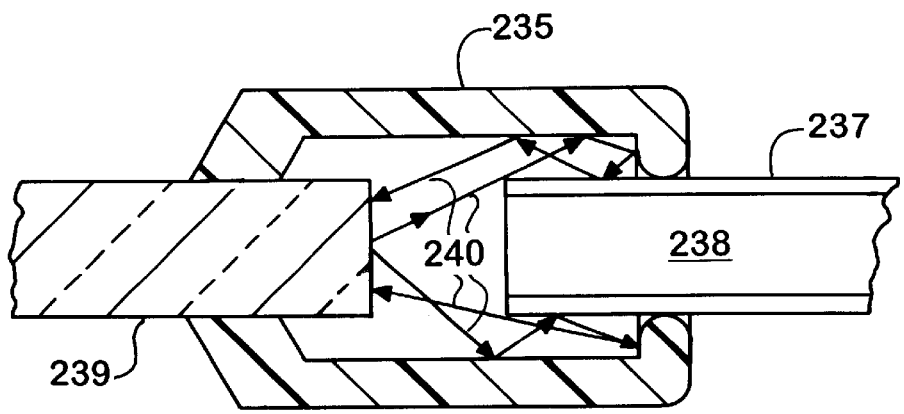
FIG. 24 illustrates an embodiment wherein light energy is directed onto a material such as a clotting agent with light-energy feedback.

The deposition of embolic coils into brain aneurysms have been the state-of-the-art therapy for certain neurovascular diseases. However, it is critical to know that the clotting agent coating is initiating the clotting process. FIG. 24 illustrates a method to use optical energy to help make such a determination. As light (indicated by arrows 240) diverges and bounces off a gripping device 235 and onto a clotting agent coating 237 (coated on coil or device 238) and back into optical fiber 239, it will change its property dynamically as the clotting of blood is initiated. The operator or physician can then determine that the local biochemistry is suitable for release. This configuration is not limited to clotting agents and can be extended to other general surface chemistry assays of interest to the physician.

Figure 25:
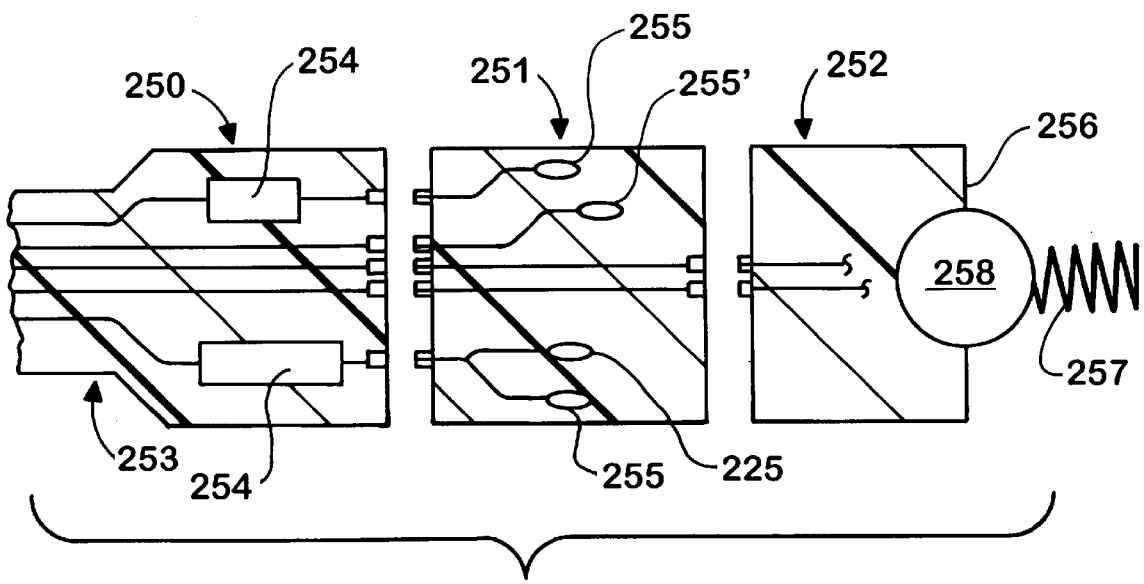
FIG. 25 illustrates an embodiment of a device comprising a power module, a sensor module and an actuator or microgripper module.

FIG. 25 illustrates an embodiment of an overall device combining a power module, a sensor module and a microgripper or actuator module. The module connections can be made via snap joints, bayonet joints, or a similar connector that maintains orientation so the electrical and optical connections can be made. As shown, the embodiment includes a power module generally indicated at 250, a sensor module 251 and a microgripper module 252. Power module 250 includes a fiber optic line/bundle (multi-line) 253 with certain of the fibers connected to photo-voltaic cells 254, with outputs of cells 254 adapted to be connected to sensors units 255 located, and certain of the fibers extend through module 250 into module 251 for connection to a sensor 255. Certain of the optical fibers extend through power module 250, sensor module 251 and into microgripper module 252, whereby light energy directed therethrough actuate a microgripper unit 256 with a deployable coil 257 via a member 258. Basically the power module 250 carries out light to electrical conversion, one or both directions, and carries out signal conditioning and has controlling electronics. The sensor module 251, for example, has electronic and optical sensors, for example, for detecting temperature, pressure, position, etc., as discussed above. The microgripper module 252 can contain release/position diagnostics including feedback, as described above.

It has thus been shown that the present invention provides modular energy conversion interfaces (photons to thermal or electrical or mechanical or acoustic) located a the distal tip of an optical fiber, enabling the design of medical devices for example, with greater utility and for less costs. The modular conversion interfaces of the present invention provides power at the distal tip of a small catheter or device, eliminates MRI incompatible materials from the medical device, reduces extraneous heating, and increases the communication bandwidth to the distal tip. The invention utilized fiber optics (5 to 400 micron diameter) to replace wires and other electrical and mechanical devices that are currently used to power, communicate and/or control medical devices, for example.

The invention can be utilized in a variety of medical applications including tethered introduction of miniature medical devices through blood vessels (cardiac, neuro and peripheral applications), through trocars for laparoscopy and arthroscopy, through needles for percutaneous applications, and directly like upper G1 or surface sensors like ECG pads or implantable/injestible devices that are tethered. Also, the invention may be useful in nondestructive evaluation of pipes, small chambers, etc.

While particular embodiments, materials, parameters, etc. have been illustrated and described to exemplify and teach the principles of the invention, such are not intended to be limiting. Modification and changes may become apparent to those skilled in the art, and it is intended that the invention be limited only by the scope of the appealed claims.

What is claimed is:

1. In a micro-mechanical system including a catheter, a fiber optic cable, a laser-light-to mechanical-power converter, and a microgripper, the improvement comprising:
    an energy conversion interface mounted at a distal end of said catheter and adjacent a distal end of said fiber optic cable, said energy conversion interface being constructed to convert photon to an energy type selected from the group consisting of electrical, thermal, mechanical and acoustic, and
    including means to convert an energy type to mechanical power.

2. The energy conversion interface of claim 1, wherein said energy conversion device comprises a device containing photo-thermal material.

3. The energy conversion interface of claim 2, wherein said photo-thermal material activates a mechanical device.

4. The energy conversion interface of claim 3, wherein said mecharnical device comprises a motor/actuator.

5. The energy conversion interface of claim 4, wherein said motor/actuator produces motion selected from the group comprising rotary motion and linear motion.

6. The energy conversion interface of claim 1, wherein said energy conversion device includes a quantity of ultraviolet sensitive material.

7. The energy conversion interface of claim 6, wherein said ultraviolet sensitive material disintegrates upon heating by light energy to a selected temperature in the range of 40° to 80° C.

8. The energy conversion interface of claim 1, wherein said energy conversion device a quantity of working fluid which produces bubbles upon heating to a temperature of 40° to 100° C. causing expansion of the working fluid for actuating a linear mechanism.

9. The improvement of claim 1, wherein said mechanical power produces motion selected from the group consisting of rotary motion and linear motion.

10. The improvement of claim 1, additionally including means for sensing at least one of the group consisting of temperature, pH, distance, pressure, position, and light intensity.

11. In a medical device including a catheter having a distal end adapted, to be connected to an electrically activated microdevice, the improvement comprising:
    at least one optical fiber having a distal end adjacent the distal end of the catheter and a proximal end operatively connected to receive laser light, and
    an energy conversion device located at said distal end of said catheter and the distal end of said at least one optical fiber and constructed to convert light energy from said optical fiber into energy of a type selected from the group consisting of electrical, thermal, mechanical, and acoustic.

12. The improvement of claim 11, additionally including sensor means activated by one or more of light energy, electrical energy, thermal energy, mechanical energy, and acoustic energy, said sensor means being constructed to sense one or more of temperature, pH, glutamate, position, distance, and light intensity.

13. An energy conversion interface, comprising:
    a least one optical fiber having a proximal end and a distal end, said distal end of said optical fiber adapted to be connected to an associated light source for directing light to the distal end of said fiber, and
    an energy conversion device operatively connected to receive light from the distal end of said optical fiber, said energy conversion device being selected from the group consisting of photons to thermal, photons to electrical, photons to mechanical, and photons to acoustic,
    said energy conversion device comprising a photo-electric transducer,
    said photo-electric transducer being operatively connected to an electrically actuated device.

14. The energy conversion interface of claim 13, wherein said electrically actuated device is selected from the group consisting of processors and sensors.

15. The energy conversion interface of claim 13, wherein said electrically actuated device comprises a sensor selected from the group consisting of pH sensors, temperature sensors, glutomate sensors, position sensors, pressure sensors, light intensity and distance sensors.

16. The energy conversion interface of claim 15, wherein said sensor is optically probed.

17. The energy conversion interface of claim 13, wherein said photo-electric transducer is operatively connected to drive a motor/actuator.

18. The energy conversion interface of claim 17, wherein said motor/actuator is constructed to produce motion selected from the group consisting of rotary and linear.

19. The energy conversion interface of claim 17, wherein said motor/actuator is operatively connected to a mechanical release mechanism.

20. The energy conversion interface of claim 13, wherein said photo-electric transducer comprises a photo-voltaic cell.

21. The energy conversion interface of claim 20, wherein said photo-voltaic cell is operatively connected to a device selected from the group consisting of microcontrollers controlling electronics units, conditioning electronics units, and source boards.

22. The energy conversion interface of claim 20, wherein said photo-voltaic cell is electrically connected to one or more components from the group consisting of resistive heating elements and bridge electrical elements.

23. The energy conversion interface of claim 22, wherein said one or more components comprises a bridge electrical element electrically connected to an electrical impedance sensor.

24. The energy conversion interface of claim 13, additionally including a member with a reflective surface, said photo-electric transducer being activated by light reflected thereon by said reflective surface.

25. The energy conversion interface of claim 24, additionally including at least another optic fiber positioned to receive light reflected by said reflective surface at its distal end for transition to its proximal end operatively connected to a point of use.

26. The energy conversion interface of claim 25, additionally including means for moving said reflective surface causing a change of intensity in light reflected by said reflective surface onto said photo-electric transducer and into said at least another optical fiber.

27. The energy conversion interface of claim 25, additionally including-a movable member which changes the intensity of the reflected light upon moving said movable member.

* * * * *